US010841737B2

(12) United States Patent
Millius et al.

(10) Patent No.: US 10,841,737 B2
(45) Date of Patent: Nov. 17, 2020

(54) APPARATUS AND METHOD FOR MINIMIZING DIRECT AND INDIRECT CROSS-CONTAMINATION OF PATHOGENS BETWEEN PERSONNEL WITHIN A WORKPLACE

(71) Applicants: Peter Millius, Atlantic Beach, NY (US); James A. White, Voorschoten (NL)

(72) Inventors: Peter Millius, Atlantic Beach, NY (US); James A. White, Voorschoten (NL)

(73) Assignee: INNOVET, LLC, Dover, DE (US)

( * ) Notice: Subject to any disclaimer, the term of this patent is extended or adjusted under 35 U.S.C. 154(b) by 0 days.

(21) Appl. No.: 16/894,030

(22) Filed: Jun. 5, 2020

(65) Prior Publication Data

US 2020/0304944 A1 Sep. 24, 2020

(51) Int. Cl.
*H04W 24/00* (2009.01)
*H04W 4/02* (2018.01)
*H04W 4/029* (2018.01)
*G08B 21/02* (2006.01)
*H04W 4/80* (2018.01)
(Continued)

(52) U.S. Cl.
CPC .......... *H04W 4/023* (2013.01); *G06K 7/1417* (2013.01); *G08B 21/02* (2013.01); *H04W 4/029* (2018.02); *H04W 4/33* (2018.02); *H04W 4/80* (2018.02)

(58) Field of Classification Search
CPC ....... H04W 4/02; H04W 64/00; H04W 4/029; G08B 21/24; G08B 25/14; H04B 5/0062; G06F 3/041; G05B 15/02; G06Q 40/08; G06Q 50/22; H04L 29/06; H04L 67/125; H04L 12/2809; H04L 67/025; H04L 12/2832; G10L 21/02; G10L 25/24;
(Continued)

(56) References Cited

U.S. PATENT DOCUMENTS 6,727,818 B1 * 4/2004 Wildman ............ G06F 19/3418
340/573.1
7,015,816 B2 3/2006 Wildman et al.
(Continued)

FOREIGN PATENT DOCUMENTS

CN 103473574 A * 12/2013

*Primary Examiner* — Mahendra R Patel
(74) *Attorney, Agent, or Firm* — Maine Cernota & Rardin

(57) ABSTRACT

An apparatus and method of minimizing pathogen cross-contamination and enhancing infection mitigation at a workplace includes placing tags at selected locations, requiring at least some workplace personnel to carry mobile devices, and logging interactions between the mobile devices and tags as tapping events. Tags can be powered or unpowered. Tapping can include RF or Bluetooth communication, and/or indicia scanning. Tapping events can be wirelessly directed to a server by the tags and/or mobile devices. The logged tapping can be used to identify high risk locations, record user movements, monitor user compliance with assigned schedules and locations, and monitor compliance with specified sanitation schedules. During mitigation of an infection event, the logged tapping can be used to identify users at high risk of direct cross-contamination due to proximity to an infected user and/or surface-mitigated cross-contamination due to occupation of a location shortly after occupation thereof by the infected user.

21 Claims, 12 Drawing Sheets

(51) Int. Cl.
*G06K 7/14* (2006.01)
*H04W 4/33* (2018.01)

(58) Field of Classification Search
CPC .... G16H 40/20; G06B 15/02; G06K 19/0723; G06K 7/10237; G06K 7/01; G06K 7/0008
USPC .............................. 455/456.1; 1/1; 340/573.1
See application file for complete search history.

(56) References Cited

U.S. PATENT DOCUMENTS

| | | | | |
|---|---|---|---|---|
| 7,242,306 | B2 * | 7/2007 | Wildman | G08B 13/2462 340/573.1 |
| 7,423,533 | B1 * | 9/2008 | LeBlond | G08B 21/245 340/572.1 |
| 8,294,584 | B2 * | 10/2012 | Plost | G08B 21/245 340/573.1 |
| 8,368,544 | B2 | 2/2013 | Wildman et al. | |
| 8,502,681 | B2 * | 8/2013 | Bolling | G16H 40/20 340/573.1 |
| 9,147,334 | B2 * | 9/2015 | Long | G08B 21/245 |
| 9,497,428 | B2 * | 11/2016 | Gaisser | H04N 5/3696 |
| 9,609,003 | B1 * | 3/2017 | Chmielewski | G06Q 40/08 |
| 9,613,518 | B2 * | 4/2017 | Dunn | G06K 9/00335 |
| 9,715,817 | B2 | 7/2017 | Wildman et al. | |
| 9,773,402 | B2 * | 9/2017 | Raichman | G08B 21/245 |
| 9,773,403 | B2 * | 9/2017 | Morgan | G08B 21/245 |
| 10,002,518 | B1 * | 6/2018 | Wheeler | G08B 21/245 |
| 10,643,446 | B2 * | 5/2020 | Kusens | G08B 21/0476 |
| 2007/0190922 | A1 * | 8/2007 | Fuchs | G21F 9/04 454/187 |
| 2009/0091458 | A1 * | 4/2009 | Deutsch | G16H 40/20 340/573.1 |
| 2011/0121974 | A1 * | 5/2011 | Tenarvitz | G08B 21/245 340/573.1 |
| 2012/0171077 | A1 * | 7/2012 | Bridges, III | A61L 2/087 422/33 |
| 2013/0187775 | A1 | 7/2013 | Marsden et al. | |
| 2014/0180713 | A1 * | 6/2014 | Tenarvitz | G16H 40/20 705/2 |
| 2014/0344953 | A1 * | 11/2014 | Roundtree | G06F 21/10 726/28 |
| 2017/0173200 | A1 * | 6/2017 | Wyman | A61L 2/0088 |
| 2019/0034820 | A1 * | 1/2019 | Manning | G06N 5/022 |
| 2020/0050995 | A1 * | 2/2020 | Ramanand | G06Q 10/06395 |

* cited by examiner

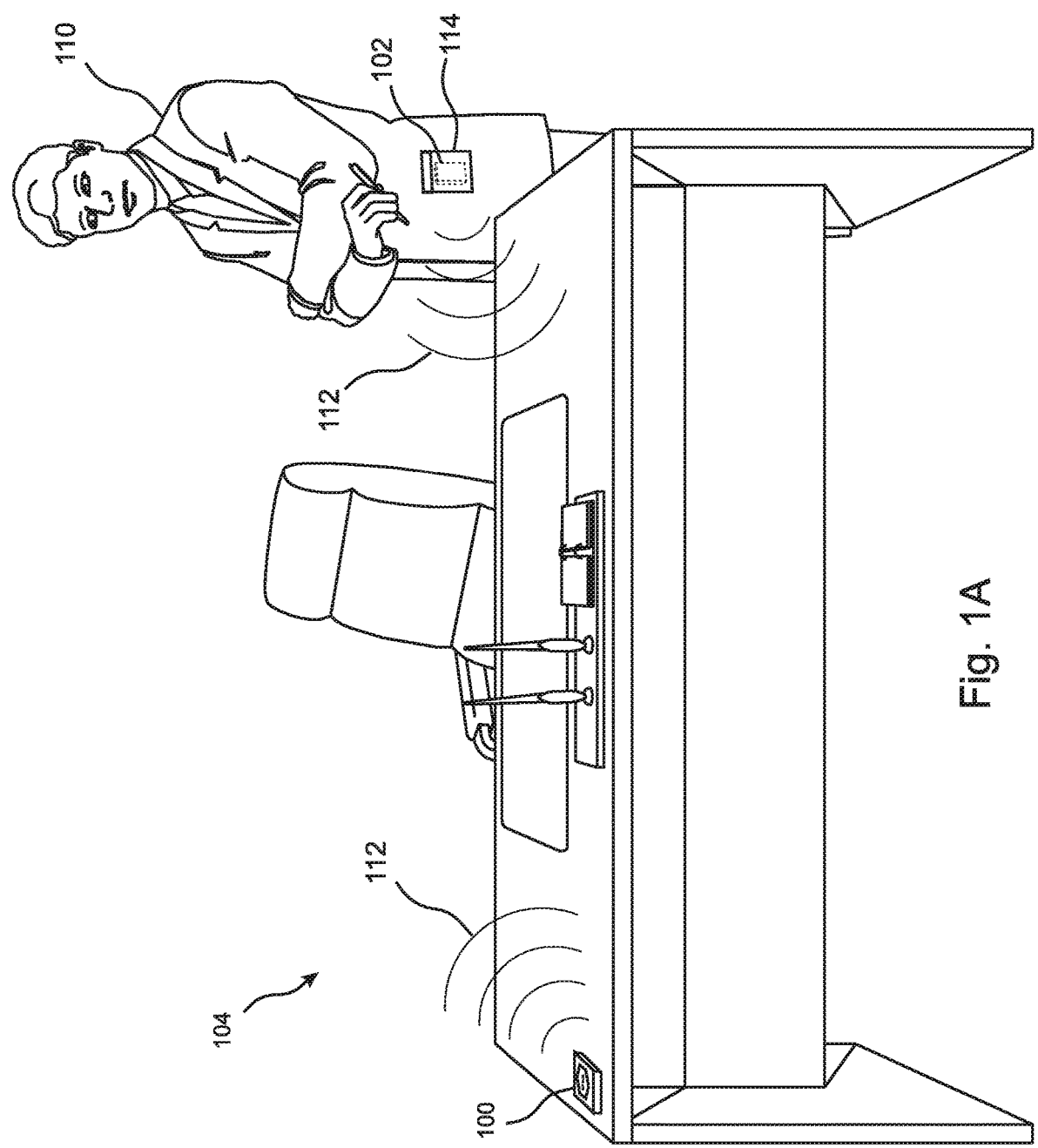

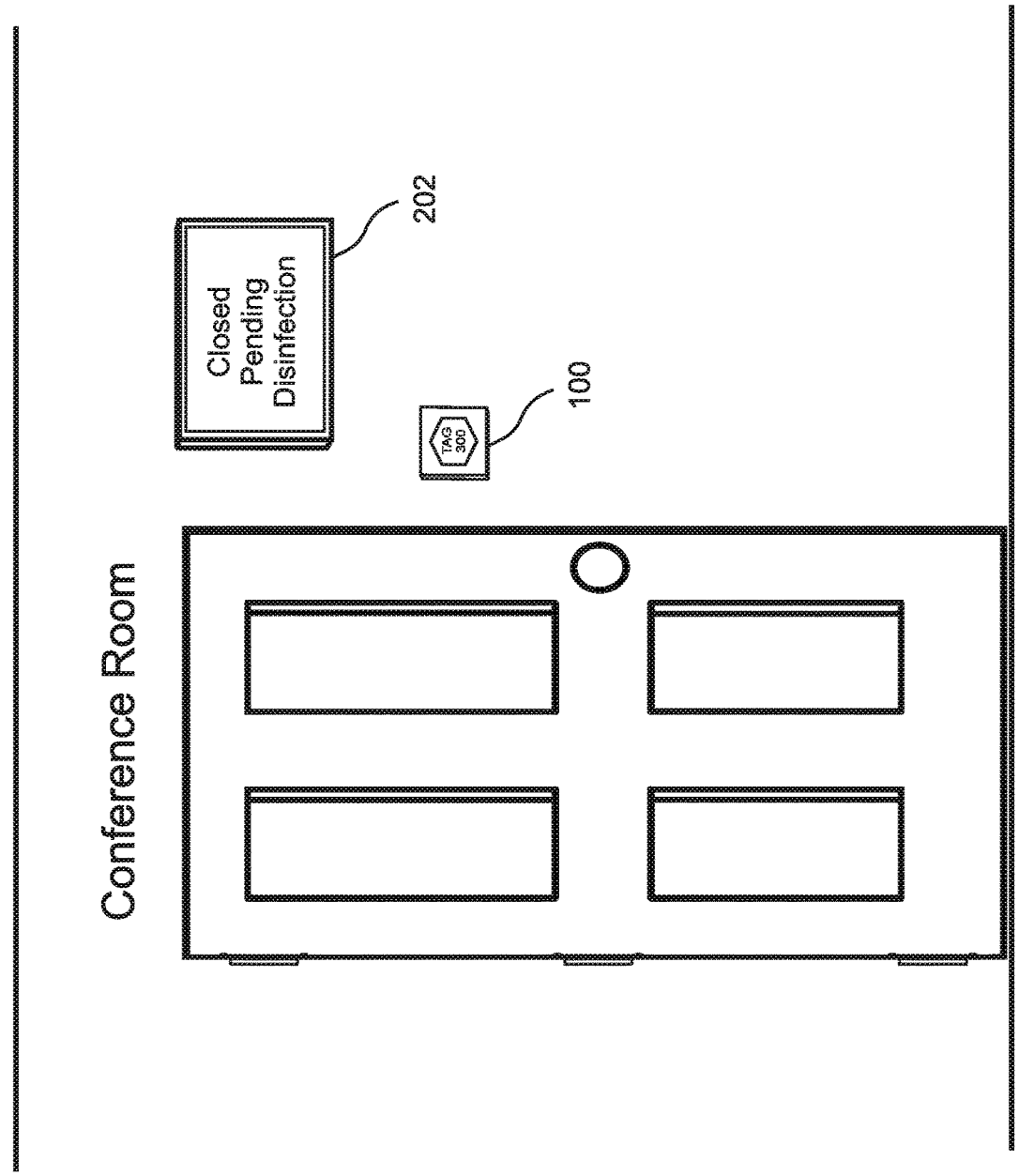

APPARATUS AND METHOD FOR MINIMIZING DIRECT AND INDIRECT CROSS-CONTAMINATION OF PATHOGENS BETWEEN PERSONNEL WITHIN A WORKPLACE

FIELD OF THE INVENTION

The invention relates to apparatus and methods for inhibiting the spread of disease, and more particularly, to apparatus and methods for minimizing cross-contamination of pathogens between personnel within a workplace environment.

BACKGROUND OF THE INVENTION

The COVID-19 pandemic, caused by the SARS-CoV-2 virus, has given rise to many new challenges. In particular, it has become clear that many business activities that are essential to the sustenance of the population, and/or to the survival of the economy, can only be carried out by employees when gathered at a workplace. Furthermore, as the incidence of SARS-CoV-2 infection has stabilized and begun to recede, it has become desirable, and even necessary in many cases, to reopen some workplaces, even though the virus has not been completely eradicated. As a result, the possibility cannot be excluded that an infectious but asymptomatic employee could be present at a workplace at any given time, and that cross-contamination of other employees could take place.

Furthermore, the emergence of SARS-CoV-2 has greatly heightened public awareness of the risks that are associated with highly transmissible infectious diseases, and of the possibility that another, more virulent strain could one day appear. Ensuring continuity of business operations under these circumstances will be critically important.

One approach is to frequently test an entire workforce for infection, in an attempt to ensure that no infected individuals are allowed to enter a workplace. However, while the capacity to test individuals for infection has grown dramatically, nevertheless it remains impractical to test every employee every day. Furthermore, only a fraction of the available testing methods are able to provide an immediate result. Accordingly, while testing can be an important tool, testing alone cannot exclude the possibility of cross-contamination at the workplace.

Testing for infection can be augmented by so-called "contact tracing," wherein the detection of an infected individual is followed by an attempt to identify all of the other individuals with whom the infected person likely had contact during a pre-symptomatic, pre-detection period when the individual was unknowingly infectious. However, this approach can be limited, because it can be very difficult to accurately determine all of the movements and activities of the infected individual prior to detecting the infection, and to comprehensively identify all of the individuals who were present at those places and times, and who also might be at risk.

Another approach is to physically isolate employees within the workplace as much as possible. While this is an important step, nevertheless in practice it is almost impossible to ensure that no two individuals in the workplace will ever be in proximity to each other, for example within six feet of each other. Furthermore, excessive separation of employees necessarily reduces the number of employees that can be present in the workplace, and can significantly reduce productivity.

In addition, the SARS-CoV-2 virus, like many other pathogens, is known to remain viable for some period of time after being deposited on surfaces, which can lead to cross-contamination even when individuals are not in close proximity to each other. One approach is to frequently sanitize all commonly touched surfaces, such as handrails, tables, desks, chairs, etc. However, sanitation to the required degree can be very time consuming, highly inefficient, and expensive, in that many surfaces may be sanitized multiple times between actual human contact events, while other surfaces may be touched many times by employees between each sanitizing. Furthermore, any lapses in implementing a thorough sanitation program could lead to otherwise avoidable cross-contamination.

What is needed, therefore, is an apparatus and method of minimizing the likelihood of both airborne and surface-mediated cross-contamination of pathogens between employees at a workplace, and for maximizing the effectiveness of contact tracing and other mitigation efforts if an infection does occur.

SUMMARY OF THE INVENTION

The present invention is an apparatus and method for minimizing the likelihood of both airborne and surface-mediated cross-contamination of pathogens between employees at a workplace, and for maximizing the effectiveness of contact tracing and other mitigation efforts if an outbreak does occur. The disclosed method and apparatus provide detailed information to the management of a workplace, both about employee usage of the facility and about sanitization activities undertaken in the facility. This detailed information, when fused with the latest scientific knowledge on the transmissibility of the disease, can provide to management the best possible data, thereby allowing them to make fully informed decisions so as to ensure the safety and productivity of the workplace staff.

According to the invention, a majority of the personnel who are present at the workplace, for example at least 80% of the personnel, and in embodiments up to 100%, are required to carry mobile devices, and critical locations within the workplace are "tagged" by strategic placement of "tags" that can be "tapped," at short range, by the mobile devices, where each tapping event represents a sensing of a tag by a mobile device or a sensing of a mobile device by a tag. Information regarding these "tapping events" is forwarded by either the mobile devices or the tags to a central server, which maintains a log "tapping events," i.e. of encounters between the mobile devices, and hence the "users" of the mobile devices, and the tagged locations. The information can be forwarded in "near-real time," i.e. each time a mobile device "taps" a location, and/or the information can be stored by the mobile devices and subsequently transmitted to the central server when a connection is established.

In various embodiments, the data that is recorded by the server includes tag identifying information, such as tag identification codes, as well as the times, and in some embodiments also the durations of the tapping events. Various embodiments determine when a user has departed a tapped location according to any of several criteria, including a "tapping out" event, noting that the same user has tapped into a different location, and/or assuming that the location has been vacated after a specified duration of time has passed, according to the type of the location, such as elevator, bathroom stall, lunch table, etc.

Of course, the locations of the tags relative to objects and structures within a building are known. This can enable an analysis of the tapping events that are logged by the server to go beyond mere proximities, and to be environmentally "aware." For example, two tapping events that take place in very close proximity may not be relevant to a contact tracing analysis if there is an intervening wall between the two tags.

Embodiments further record specific information regarding the nature or "type" of the tapping event, for example "arrived at location," "sanitized location," "departed location," and "mark location as a frequently visited point." Selection of the type of tapping event can be made by the user selecting from among a plurality of tags, and/or by the user selecting an icon or otherwise entering information into the mobile device.

In some embodiments, the tags are devices that are powered, for example by small batteries, and can be sensed by any of the mobile devices that is within a specified distance of the tag, such as within six feet. In some of these embodiments, the communication between the tags and the mobile devices is, or can be, via Bluetooth, where the Bluetooth range of the tags can be limited, for example by limiting the power that is supplied to the Bluetooth transmitter of the tag. For example, the tag can be a Bluetooth "beacon" that is sensed by a cellular telephone that is serving as the mobile device by running an app that is specific to implementing the present invention, where the cellular telephone is in network communication with the server. Or, the tag can be a Bluetooth-enabled device that is in network communication with the server, while the mobile device is a Bluetooth beacon. In the latter case, the "tag" can be an electronic display that is able to display messages to users according to instructions received from the server.

This approach of using powered, Bluetooth-enabled tags can be desirable for certain environments within a workplace, such as within elevators or when monitoring the sanitation of hotel rooms. Certain of these embodiments support automated, "passive tapping," in that the mobile devices automatically communicate with the tags whenever a "user" comes within range of a tag. According to this approach, the tags can be placed in obscure, unobtrusive locations, and users need not be aware of the locations of the tags.

In other embodiments, the tags are unpowered. For example, the tags can be scannable labels or objects, such as "QR" codes, near-field communication devices (NFC's), or RFID's that are unpowered except when one of the mobile devices is located very nearby, such as within one foot, whereupon the tags are powered by RF energy emitted by the mobile devices. This approach eliminates any need to periodically replace the tags, or to replace batteries in the tags. However, this approach typically requires "active tapping," wherein users "tap in" to a location by intentionally placing their mobile devices into proximity of a tag, either to scan a code or to energize an NFC device, each time the individual arrives at a tagged location. In some embodiments, users are also required to "tap out" of locations by placing their mobile device into proximity of a tag when they depart from a location.

Embodiments can combine within the same workplace both powered and unpowered tags, and can combine both passive and active tapping. For example, actively tapped (scanned) QR-code tags may be used at strategic locations within each floor of an office building, while passively tapped, Bluetooth beacons may be implemented in elevators of the same building.

Method embodiments of the present invention implement the devices that are described above, and then make use of the logged information by implementing any or all of the following methods.

Determining Location "Risk"

Embodiments determine a degree of risk of a tagged location, for example "low risk", "medium risk" or "high risk," according to whether any users have "tapped" the location since it was most recently sanitized. In some embodiments, a location is also deemed to be "low risk" after a certain duration of time has elapsed since it was most recently tapped, even if the location has not been sanitized in the meantime. Embodiments further indicate degrees of risk for various locations, such as a "moderate risk" rating when sufficient time has elapsed since the most recent tapping to cause most or all pathogens, if present, to have become non-viable. Embodiments push messages to the mobile devices to indicate the risk status of locations, for example to inform a user of a desk as to whether the desk location is considered to be low risk.

Sanitation Quality Control

According to embodiments of the present invention, sanitation personnel within the workplace are required to carry mobile devices, and their encounters with tags are logged. In some embodiments that require active tapping, sanitation workers are required to "tap in" when they arrive at a location that is to be sanitized, and this information is logged and used to ensure that an established sanitation schedule is adhered to. In some of these embodiments, the duration of the worker's encounter with a location is determined and recorded, either by requiring the worker to "tap out" when the sanitation is completed, and/or by noting when the worker taps into another location.

Embodiments further record whether a location was merely "sanitized,", or if the location was "disinfected" or "sterilized." The determination can be according to work instructions given to sanitizing personnel, and/or information provided by the sanitation personnel. Embodiments further record specific products and chemicals that are used for sanitation, for example by directing sanitation workers to scan barcode labels provided on product containers using their mobile devices.

Here "sanitized" refers to a combination of cleaning, i.e. removing visible dirt and debris, in addition to treatment with one or more substances that kill bacteria, but not necessarily viruses or fungi. "Disinfected" refers to a treatment with one or more substances that reduce or effectively eliminate viruses and fungi, in addition to bacteria. "Sterilization" refers to a treatment that destroys all microscopic life, and can include treatment by chemicals, heat, and/or radiation such as ultra-violet light.

Determining User Movement Patterns

In embodiments, during an initial tracking phase, users are allowed to move between workstations, bathrooms, and eating or other common areas, without restriction, and their movements are monitored according to the tapping events that are logged. Subsequently, in some embodiments, users are only required to tap in at locations that are outside of their normal movement patterns. For example, during normal hours of usage, after the initial tracking phase, a user may not need to continue tapping his or her desk and preferred lunch table, which the user encounters at the same times each day, but may still be required to tap in at conference rooms when attending meetings that are not daily events. In some of these embodiments, a "geo-fence" approach can be used to determine if a user is present at the workplace on a given day, for example based on determining the user's location using "GPS" (global positioning system) location awareness.

In some embodiments, users are encouraged or assigned to use certain specified bathroom stalls, sinks, cafeteria tables, and other locations at certain specified times. This approach can help to avoid crowding of certain locations by ensuring that use of common facilities such as bathroom stalls, lunch tables, etc. is distributed over time and among personnel. This approach can reduce each user's "virus footprint," i.e. the range of locations and personnel who would be placed at risk if the user were to be unknowingly infectious.

Focusing Mitigation Efforts

In embodiments, if a user is found to have been infected, the logged tapping information can be used to enhance contact tracing by focusing testing and other mitigation efforts on other users who were either proximal to the infected user, e.g. ate at the same lunch table, or who were most likely to have come into contact with a surface that was touched by the infected user, e.g. used the same bathroom stall shortly after the infected user. In embodiments, air current patterns are assessed in common areas such as dining areas, bathrooms, and cubical "farms," and are used to estimate which personnel located in these areas are most likely to be infected by air-born virus particles emitted by an infected user.

Defining "Sub-Groups" of Personnel

By assigning certain bathroom stalls, sinks, lunch tables, and other common areas to the same limited group of users, embodiments create virtual sub-groups of users who come into some limited contact with each other, either in person or via shared surfaces, but who rarely come into contact with any other users outside of their sub-group. Accordingly, if a user is found to be infected, testing and other mitigation efforts can be rendered more effective by focusing these efforts primarily on the other members of the infected user's sub-group. Furthermore, in the worst case, any spread of the infection is likely to be limited only to other personnel within the sub-group, or to only a few sub-groups, and is less likely to spread throughout the workforce as a whole.

The present invention is a method of minimizing cross-contamination of pathogens between personnel located at a workplace and/or improving an efficacy of a response to a cross-contamination at the workplace. The method includes locating a plurality of tags at selected tagged locations within the workplace, selecting a majority of all of the personnel who are present at the workplace to be protected personnel, for each protected person of the protected personnel, causing the protected person to maintain a mobile device in the protected person's possession while the protected person is in the workplace, said mobile device being configured to interact with each of the tags during a tapping event when the mobile device is proximal to the tag, at least one of the mobile devices and the tags being configured to provide tapping information regarding said tapping events to a server, and according to an analysis of the tapping information, taking an action that reduces a risk of cross-contamination of pathogens between the personnel who are present at the workplace by modifying at least one activity of at least one of the protected persons, and/or enhances an efficacy of a response to a cross-contamination at the workplace by identifying at least one of the protected persons who is at an enhanced risk of cross-contamination.

In embodiments, the protected personnel include at least 80% of all of the personnel who are present at the workplace.

In any of the above embodiments, the tags can be powered devices. In some of these embodiments, the tags are configured to communicate with the mobile devices by Bluetooth communication. Or the tags can be unpowered. In some unpowered embodiments the tags are configured to communicate with the mobile devices by near field communication.

In any of the above embodiments, the tags can include optically scannable indicia.

In any of the above embodiments, the tapping information can include information pertaining to a duration of time during which the protected person was proximal to the tag.

In any of the above embodiments, the mobile devices can be configured to accept input information provided by the protected personnel, and to include said input information with the tapping information. In some of these embodiments, the input information includes information relevant to sanitation of the location where the tag is located.

In any of the above embodiments, modifying the at least one activity of the at least one protected person can include causing a first of the protected persons to avoid a tagged location by designating the tagged location as being at elevated risk if, according to the tapping information, the tagged location has not been sanitized since it was previously tapped by a second of the protected persons, and insufficient time has elapsed since the tagged location was tapped by the second of the protected persons to ensure that a specified percentage of any pathogens deposited at the tagged location by the second of the protected persons have become non-infectious.

In any of the above embodiments, modifying the at least one activity of the at least one protected person can include causing the protected person to adhere to sanitization requirements that are assigned to the protected person, if the analysis of the tapping information indicates non-compliance therewith.

In any of the above embodiments, modifying the at least one activity of the at least one protected person can include directing the protected person to consistently use a designated facility from among a plurality of facilities that are within the workplace. In some of these embodiments, the designated facility is selected from among the plurality of facilities according to an analysis of the tapping information obtained before the designated facility was selected in any of these embodiments, the method can further include dividing the protected persons into a plurality of sub-groups, and assigning the plurality of facilities that are within the workplace to the subgroups, such that use of the same one of the facilities by members of more than one of the subgroups is minimized or eliminated. And in some of these embodiments, the plurality of facilities includes facilities that are located in a plurality of common areas.

In any of the above embodiments, enhancing the efficacy of the response to the cross-contamination at the workplace can include, upon determining that a first protected person of the protected persons is infected with a pathogen, analyzing the tapping information to identify a second protected person of the protected persons who is at heightened risk of cross contamination of the pathogen by the first protected person, and applying at least one mitigating action to the second protected person. In some of these embodiments, the mitigating action is applying a test to the second protected person to determine if the second protected persons has become infected with the pathogen. In any of these embodiments, identifying the second protected person can include determining that the second protected person occupied a location that was previously occupied by the first protected person, said occupation by the second protected person being at a time when a heightened risk existed of cross contamination of the second protected person due to touching a surface that had previously been contaminated by the first protected person. In any of these embodiments, identifying the second protected person can include determining that the first and second protected persons occupied the same or proximal locations within the workplace at the same time. And in some of these embodiments identifying the second protected person can further include determining a pattern of air currents proximal to the location or locations within the workplace that were occupied by the first and second protected persons at the same time.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 1A is a perspective view of an employee workstation within a workplace according to an embodiment of the present invention where a Bluetooth beacon has been applied to a desk as a tag and a worker is carrying a mobile device in his pocket;

FIG. 3B is a front view of an entrance to a conference room where a tag has been applied and where an electronic sign has been installed that presents information regarding availability of the conference room as directed by the server in an embodiment of the present invention;

DETAILED DESCRIPTION

Figure 1B:
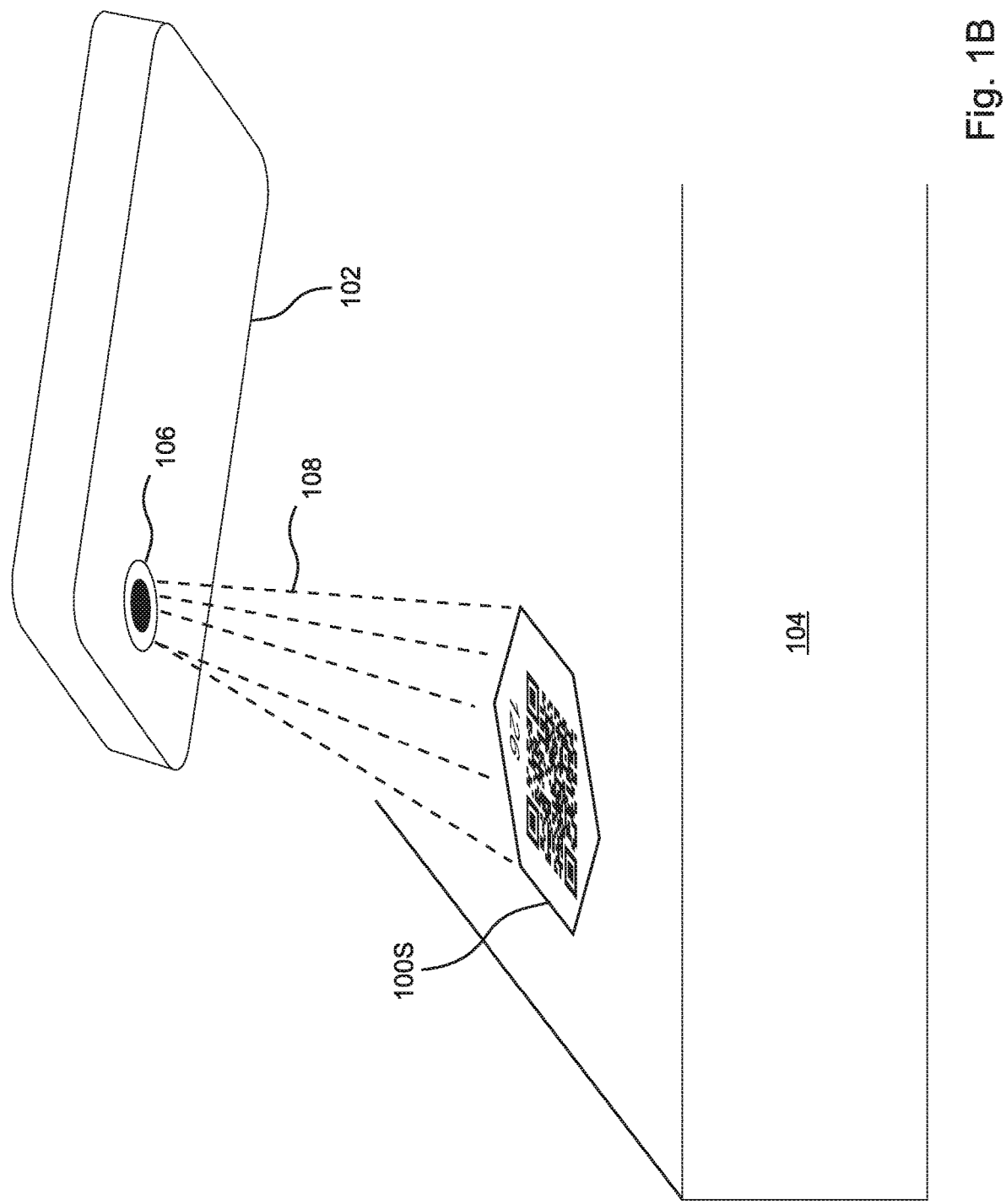
FIG. 1B is a perspective view of a mobile device scanning a tag that displays a QR-code in an embodiment of the present invention.

The present invention is an apparatus and method for minimizing the likelihood of both airborne and surface-mediated cross-contamination of pathogens between employees at a workplace, and for maximizing the effectiveness of contact tracing and other mitigation efforts if an infection does occur.

With reference to FIG. 1A, according to the present invention a majority of the personnel 110 who are present at the workplace, for example at least 80% of the personnel 110, and in embodiments up to 100% of the personnel 110, are required to carry mobile wireless devices 102. The mobile devices 102 are able to interact with "tags" 100 that are located at key locations within the workplace, such as desks 104 used by employees. These interactions, or "tapping events," can include scanning or sensing of tags by the mobile devices and/or scanning or sensing of the mobile devices by tags. The scanning or sensing is generally limited to only short-range detection, so that each tapping event indicates proximity of the tag 100 to the mobile device 102, and hence of the "user" 110 who is carrying the mobile device 102.

In the embodiment of FIG. 1A, the tag 100 is a Bluetooth beacon that is attached to a user's desk 104, while the mobile device 102 is a cellular telephone. The Bluetooth range of the tag 100 is limited by limiting the power that is supplied to the Bluetooth transmitter of the tag 100, and thereby limiting the power of the RF signal 112 that is emitted by the tag 100. In similar embodiments, the tag 100 is a Bluetooth-enabled device that is in network communication with the server, while the mobile device 102 is a Bluetooth beacon. This approach of using powered, Bluetooth-enabled tags can be even more desirable for other environments within a workplace, such as within elevators. In embodiments where it is impractical to limit the Bluetooth detection range, the location of a user can be estimated by analyzing simultaneous tapping events recorded between a mobile device and a plurality of tags.

Embodiments such as FIG. 1A support automated, "passive tapping," in that the mobile device 102 and tag 100 automatically communicates with each other whenever the user 110 comes within range of the tag 100, without requiring the user 110 to take any specific action. In the illustrated example, the mobile device 102 can communicate with the tag 100 while remaining in the user's pocket 114. In some of these embodiments the tags can be placed in obscure, unobtrusive locations (although the tag 100 in FIG. 1A is located in a clearly observable location), and users 110 need not be aware of the locations of the tags 100.

Figure 1C:
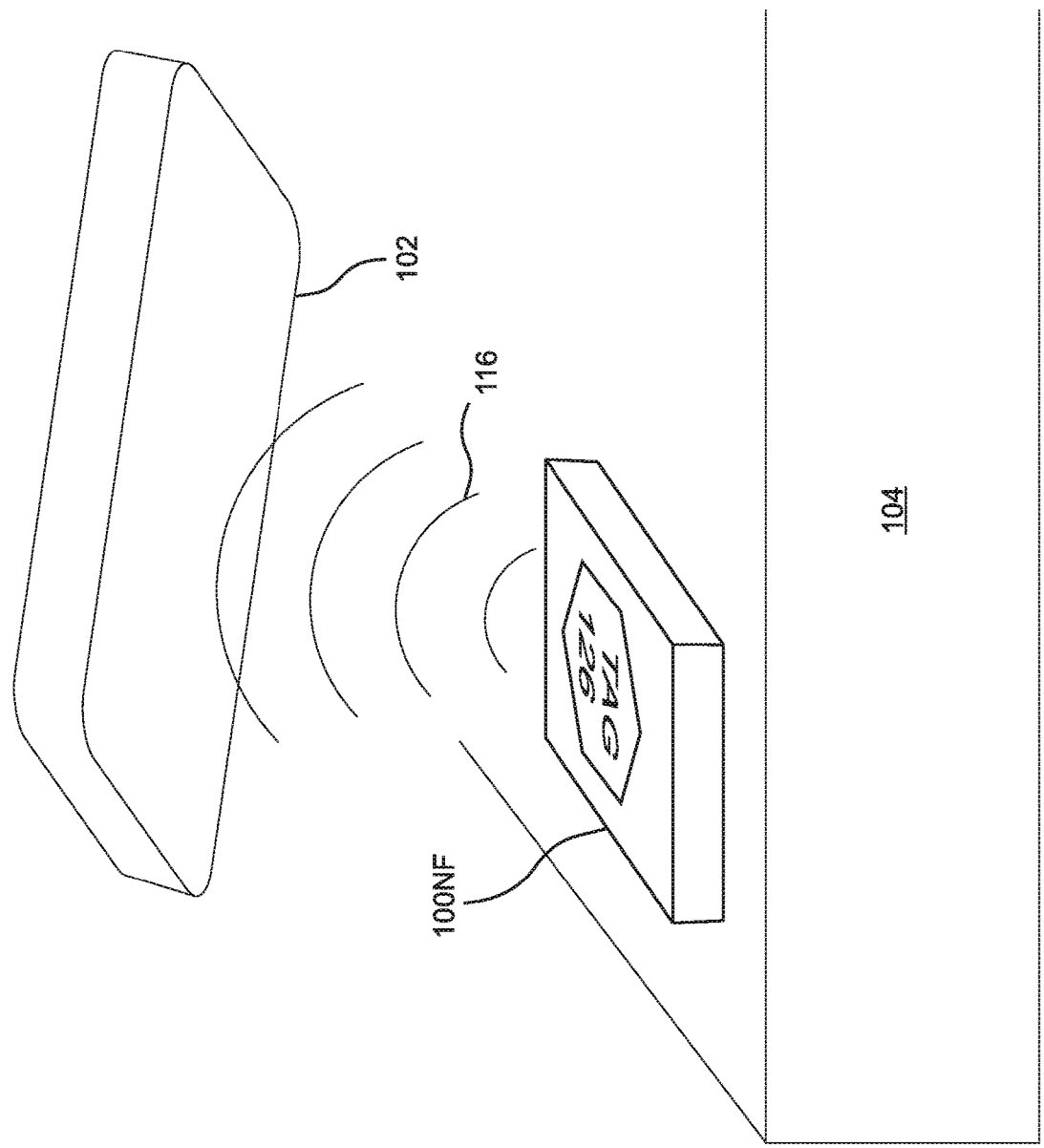
FIG. 1C is a perspective view of a mobile device receiving information from a near field RF tag that is energized temporarily by the mobile device in an embodiment of the present invention.

With reference to FIGS. 1B and 1C, in other embodiments the tags 100 are labels or objects 110S such as "QR" codes (FIG. 1B), that can be scanned 108 by a camera 106 included in the mobile device 102, and/or are near-field communication devices (NFC's) or RFID's 100NF (FIG. 1C) that are unpowered except when one of the mobile devices is located very nearby, such as within one foot, whereupon the tags 100NF are powered by RF energy 116 emitted by the mobile devices 102. This approach eliminates any need to periodically replace the tags 100, or to replace the batteries in the tags 100. However, this approach typically requires "active tapping," wherein users 110 "tap in" to a location by intentionally placing their mobile device 102 into proximity of a tag 100, either to scan 108 a code 100S or to energize 116 an NFC device 100NF, each time the individual 110 arrives at a tagged location. In some embodiments, users 110 are also required to "tap out" of locations by placing their mobile device 102 into proximity of a tag 100 when they depart from a location.

Figure 1D:
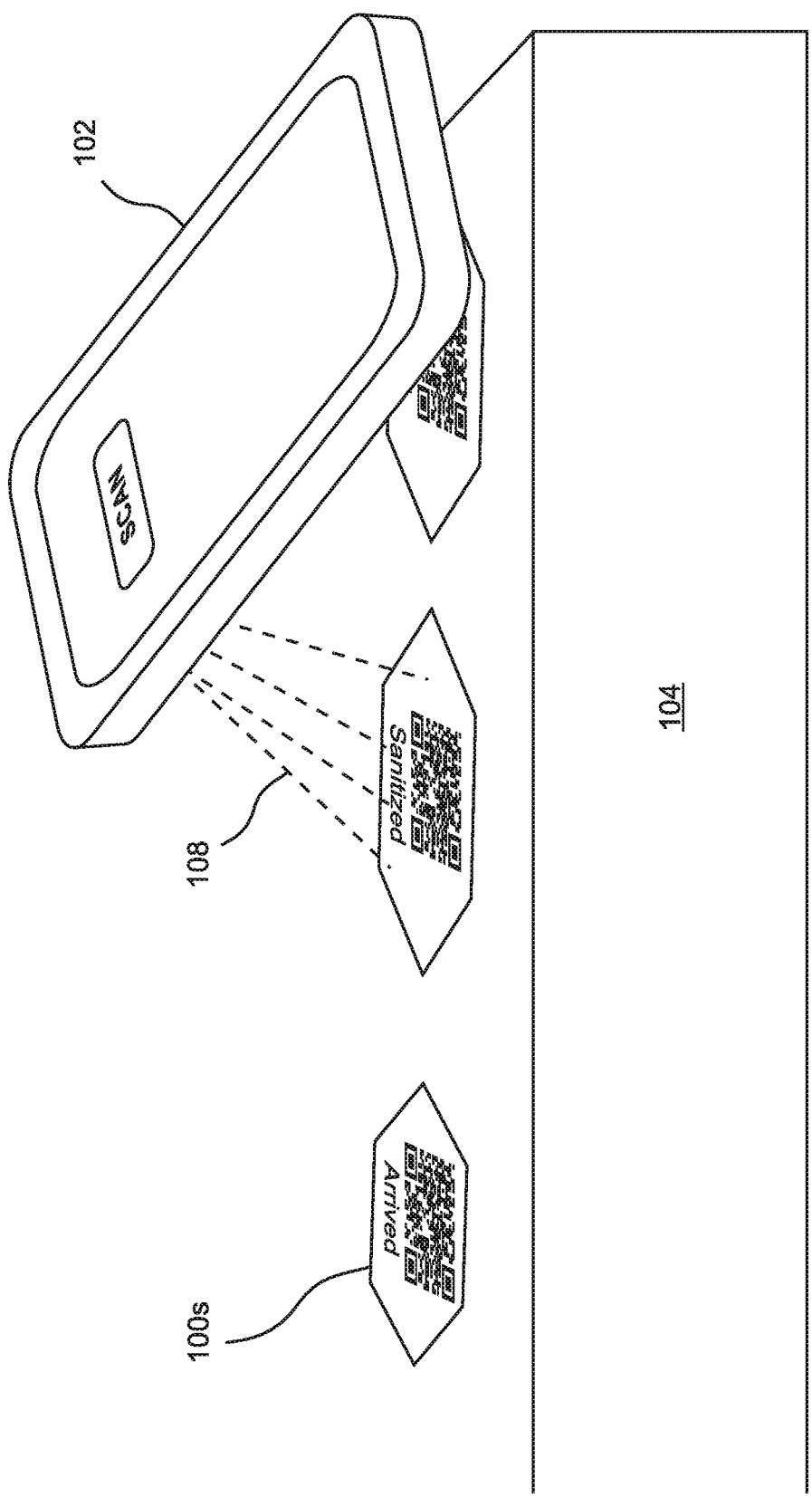
FIG. 1D is a perspective view of a mobile device scanning a selected one of a plurality of tags applied to a desk in an embodiment of the present invention.
Figure 1E:
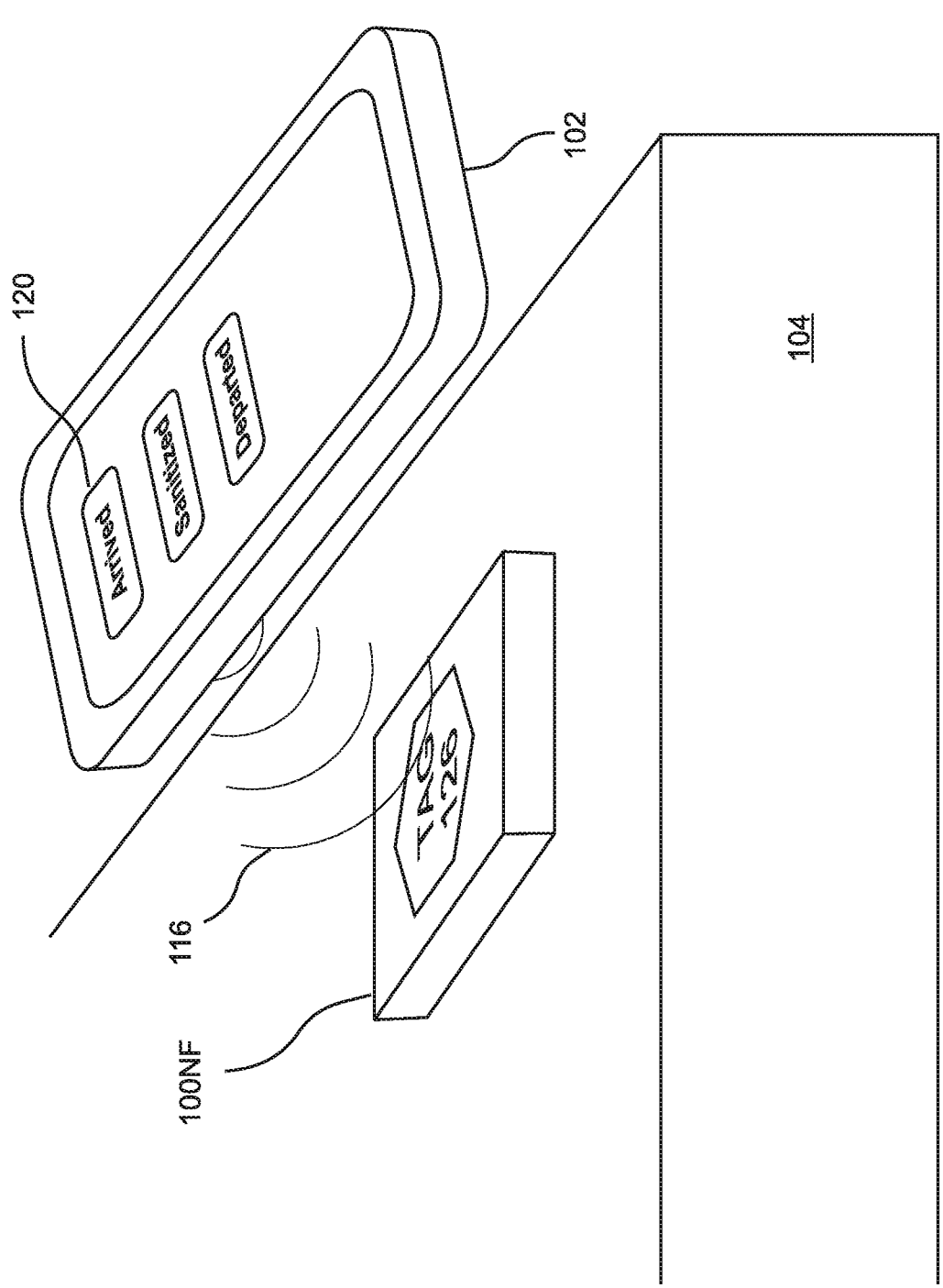
FIG. 1E is a perspective view of a mobile device presenting a menu of tapping information during a tapping event for selection by a user in an embodiment of the present invention.

Embodiments further record specific information regarding the nature or "type" of the tapping event, for example "arrived at location," "sanitized location," "departed location," and "mark location as a frequently visited point." Selection of the type of tapping event can be made by the user selecting from among a plurality of tags 100S, as illustrated in FIG. 1D, and/or by the user selecting an icon 120 or otherwise entering information into the mobile device 102, as illustrated in FIG. 1E.

Figure 2:
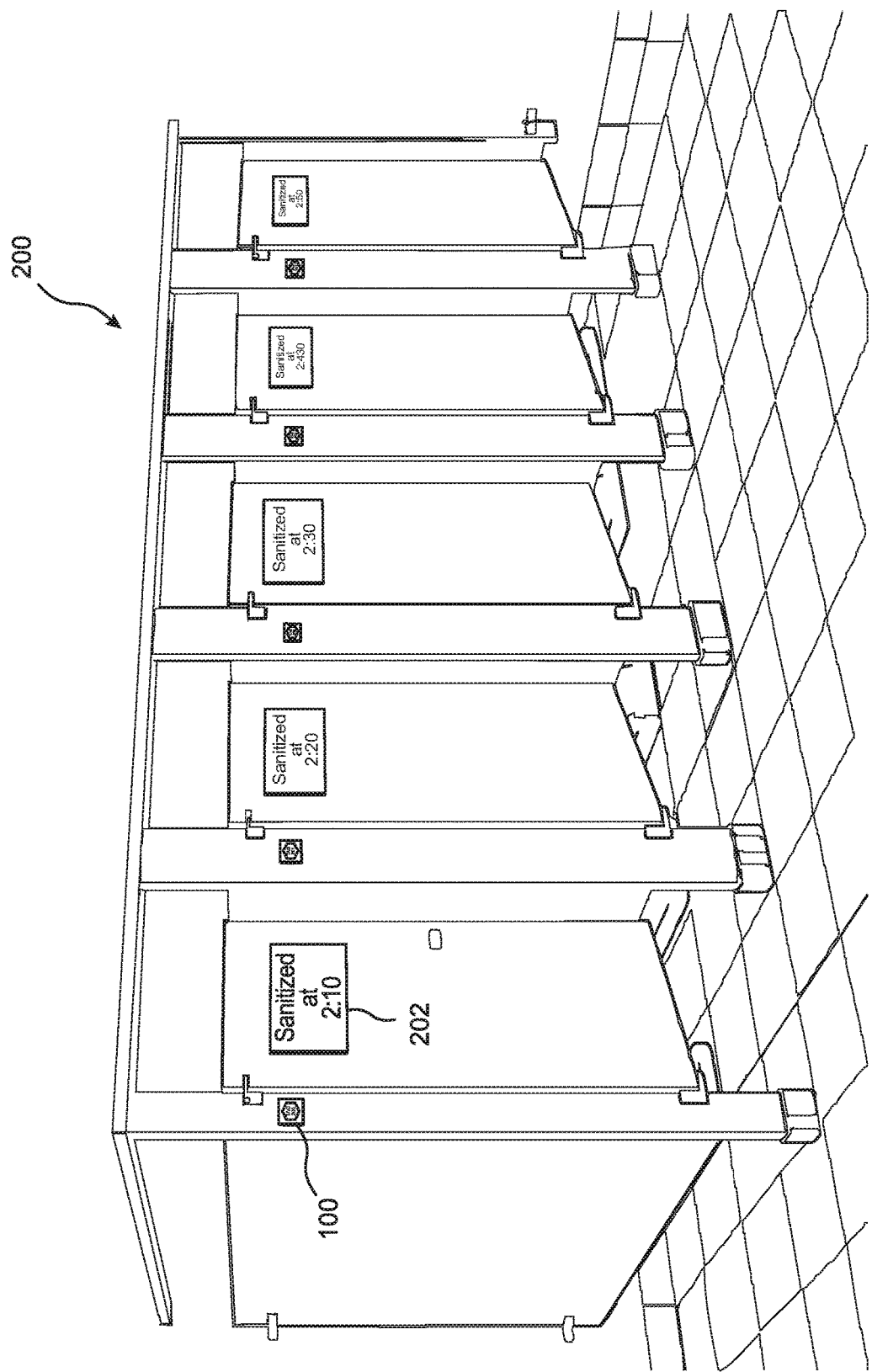
FIG. 2 is a perspective view of a plurality of bathroom stalls having associated tags and electronic displays that present information pertaining to sanitizing of the stalls in an embodiment of the present invention.
Figure 3A:
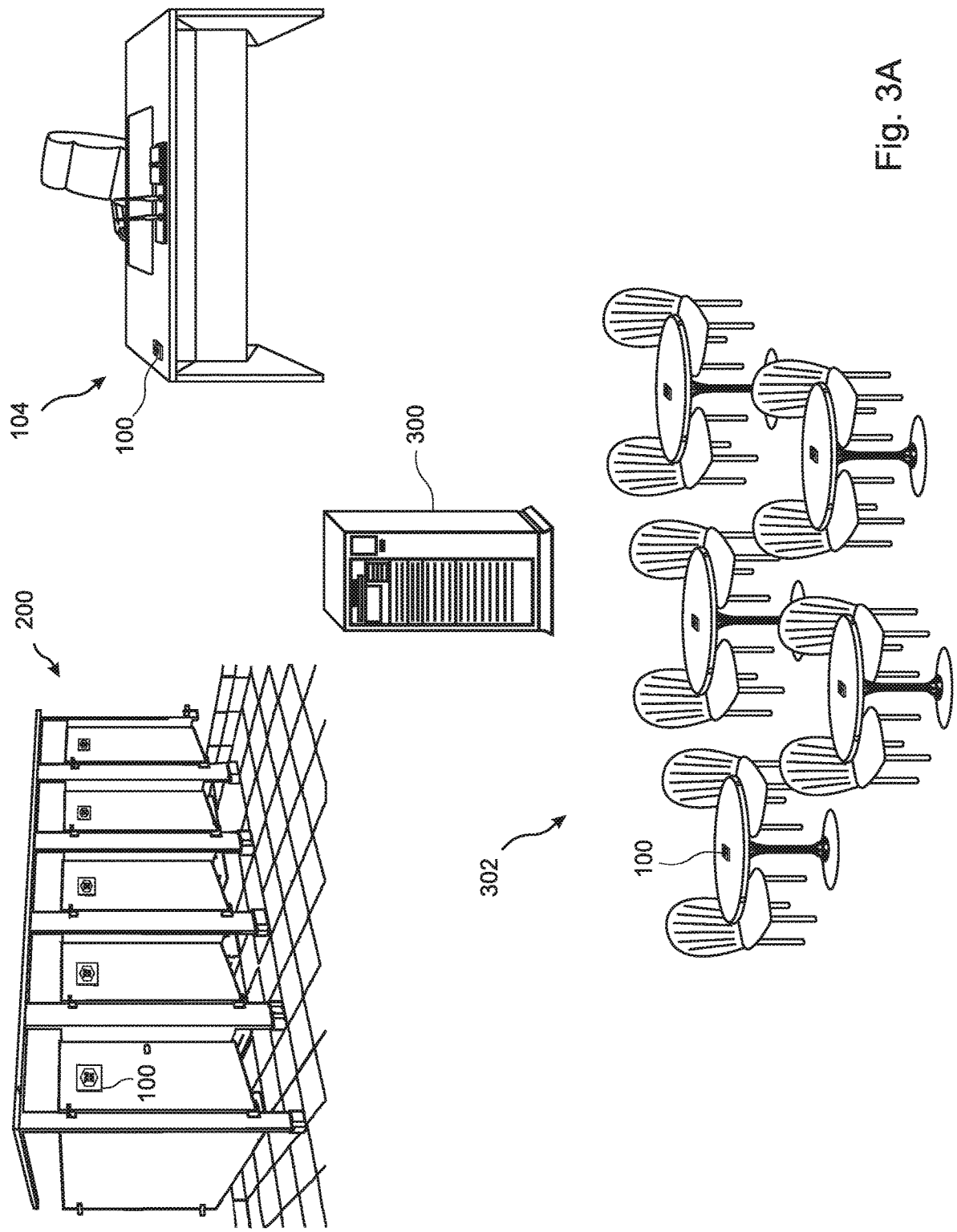
FIG. 3A is a perspective view of a server positioned to receive tapping information relevant to a plurality of tagged locations within a workplace in an embodiment of the present invention.

With reference to FIG. 2, tags 100 are also placed at key locations within common areas, such as bathroom stalls 200 and sinks (not shown), as well as handrails in hallways (not shown) and tables in dining areas (302, FIG. 3A).

With reference to FIG. 3A, information regarding tapping "events" is forwarded by the mobile devices 102 and/or by the tags 100 to a central server 300, which maintains a log of encounters between the mobile devices 102, and hence the "users" 110 of the mobile devices 102, and the tagged locations. The information can be forwarded in "near-real time," i.e. each time a mobile device 102 "taps" a location, and/or the information can be stored by the mobile devices 102 or tags 100 and subsequently transmitted to the central server 300 when a connection is established. In embodiments the server 300 records the times when the encounters took place, and in some embodiments also the durations of the encounters.

With reference again to FIG. 2, and with reference to FIG. 3B, electronically controlled signage 202 such as "e-ink" displays can be used to display the current status of a common area facility, such as a bathroom stall, as determined from tapping information that is logged by the central server 300. For example, with reference to FIG. 3B, during contact tracing after an infection event, if it is discovered that a conference room has been recently occupied by an individual who is likely to have been infected, then the conference room may be designated as being closed until it can be thoroughly disinfected.

In another example, electronically controlled signage 202 can be installed within or at the entrances of hotel rooms, and can display updated disinfection information to hotel guests. The signage 202 can include Bluetooth receivers and can be in network communication with the server 300, whereby the signage 202 function as tags 100, so that cleaning personnel need only carry Bluetooth beacons as their mobile devices 102. If it is not convenient to restrict the Bluetooth communication range of the signage 202, then in embodiments the location of a room sanitizing employee is determined to a high degree of accuracy by analyzing the times of signal detection and, in some embodiments the signal strengths that are reported to the server 300 by a plurality of the signage devices 202.

Method embodiments of the present invention collect and log information pertaining to tapping events as described above, and then make use of the logged information by implementing any or all of the following methods.

Determining Location "Risk"

Figure 4:
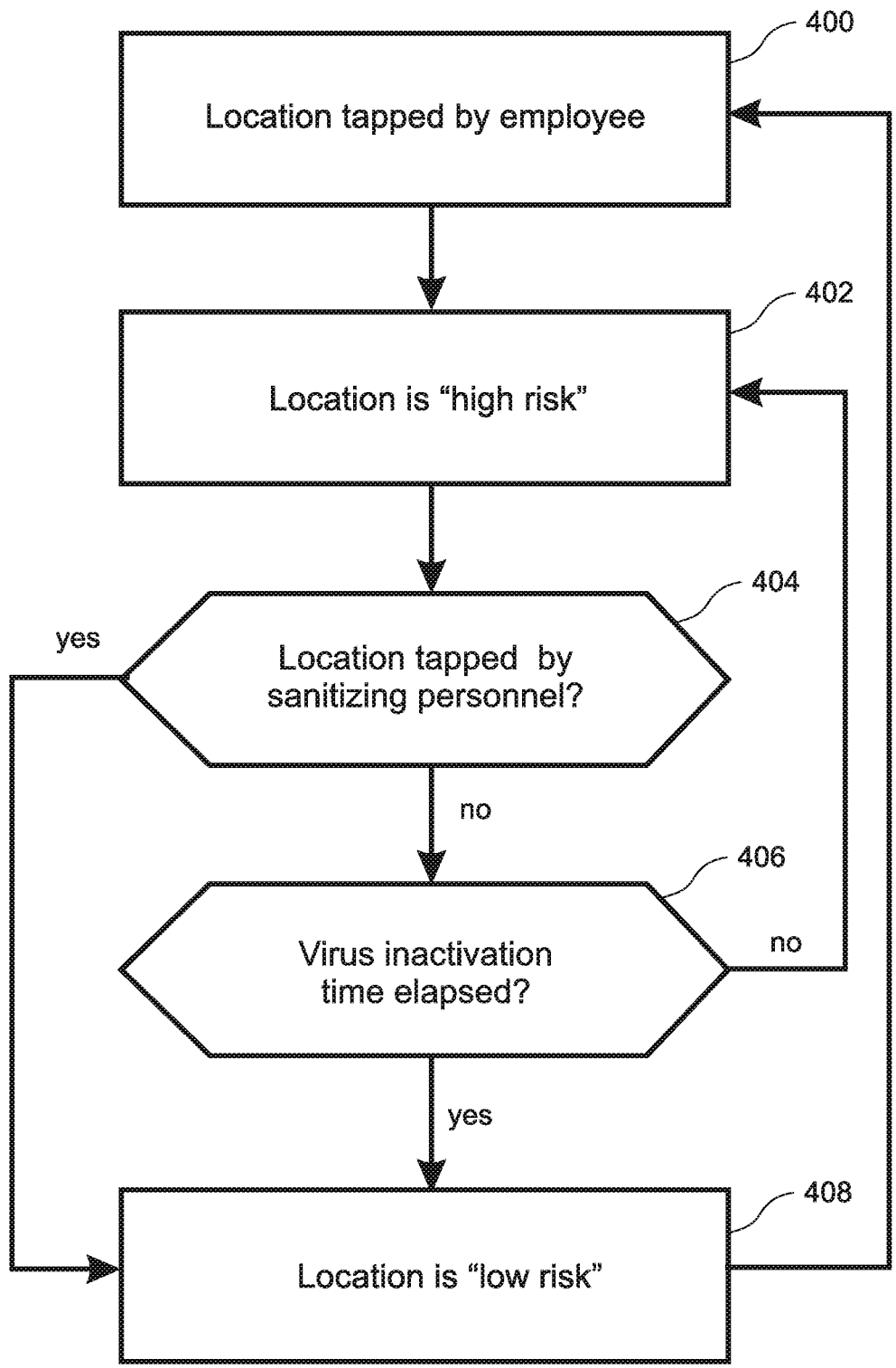
FIG. 4 is a flow diagram illustrating a method embodiment of the present invention wherein a degree of risk of a location is determined according to logged tapping events.

In embodiments, the information logged by the server 300 is used to determine a degree of risk of a tagged location, such as "low risk", "medium risk" or "high risk," according to whether any users 110 have "tapped" the location since it was most recently sanitized. In some embodiments, with reference to FIG. 4, when a server 300 is informed that a location has been tapped 400 by a "high risk" user 110, the server 300 initially deems the location to be "high risk" 402 for contact with other users. If the location is subsequently tapped by a sanitization worker, and if the tapping indicates that the sanitation worker completed a sanitation of the location, or at least remained at the location for a duration that is consistent with a sanitizing event, then the location is deemed to have been sanitized and to be "low risk" 408.

In some embodiments, users 110 are assigned to sanitize their own workstations 104 before they depart, and to confirm that they have performed this task when they "tap out" from the workstation 104, for example by tapping a specific tag 100, and/or by entering information into their mobile device 102. Upon receiving this information, the server 300 then designates the workstation 104 to be low risk for use by another user 110, for example for an employee 110 who shares the same workstation 104 but during a different work shift.

If the server does not receive any information indicating that a location has been sanitized 404, then the server 300 continues to deem the location to be high risk until sufficient time has elapsed 406 to cause any deposited pathogens to become inactivated, at which point the server 300 deems the location to be low risk 408, even if it has not been sanitized since the previous user encounter 400. Embodiments further indicate degrees of risk for various locations, such as a "moderate risk" rating when sufficient time has elapsed since the most recent tapping to cause most pathogens, if present, to have become non-viable.

Embodiments push messages to the mobile devices 102 of users, and/or to strategically located electronic displays 202, to indicate the safety status of locations, for example to inform a user 110 whether an unoccupied conference room (e.g. FIG. 3B) is considered to be low risk. In some embodiments, if a second user 110 taps into a location that is considered to be high risk due to a recent interaction with a first user 110, then a warning alert is transmitted by the server 300 to the mobile device 102 of the second user 110 so as to warn the second user 110 to take appropriate measures as dictated by organizational policies and procedures, such as to evacuate the area until it is deemed low risk.

Sanitation Quality Control

Figure 5:
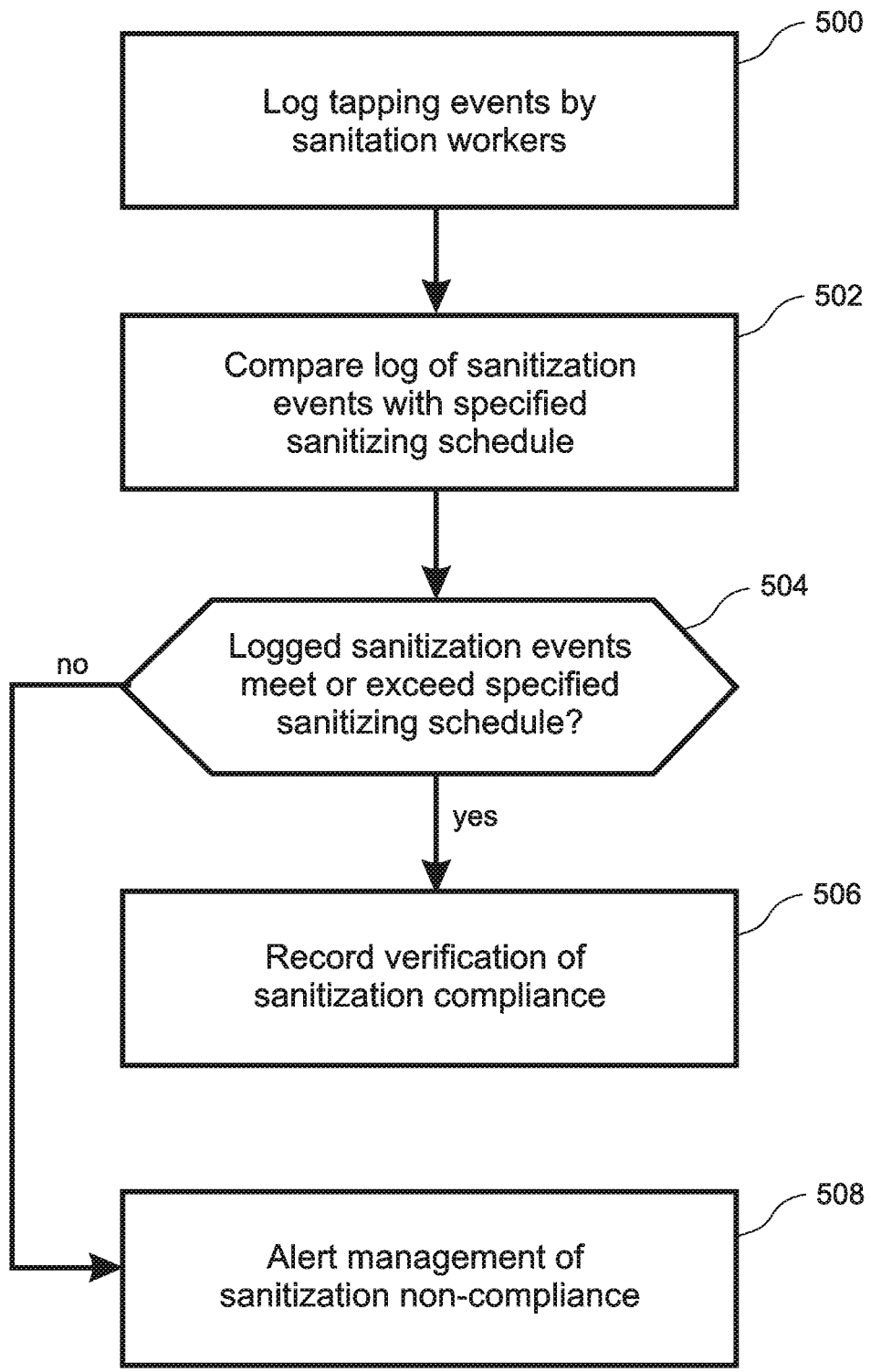
FIG. 5 is a flow diagram illustrating a method embodiment of the present invention wherein logged tapping events are analyzed to determine compliance with a specified sanitation schedule.

According to the present invention, sanitation personnel within the workplace are required to carry mobile devices 102, and with reference to FIG. 5 their encounters with tags 100 are logged 500. In some embodiments, the logging further indicates whether a sanitation was performed, or at least whether the sanitation worker remained at the location for a duration that is consistent with a sanitizing event.

Embodiments can send push notifications to facility managers when scheduled sanitization activities do not occur according to schedule. In these cases, the system can automatically increase the risk associated with the particular tagged location based on utilization by staff, and/or until proper sanitization has been undertaken. In embodiments the algorithms that are used to assess risk are stored in the central server, and can be updated according to the latest scientific understanding of one or more pathogens that may be present in the environment.

Embodiments further record whether a location was merely "sanitized,", or if the location was "disinfected" or "sterilized." The determination can be according to work instructions given to sanitizing personnel, and/or information provided by the sanitation personnel. Embodiments further record specific products and chemicals that are used for sanitation, for example by directing sanitation workers to scan barcode labels provided on product containers using their mobile devices 102.

Here "sanitized" refers to a combination of cleaning, i.e. removing visible dirt and debris, in addition to treatment with one or more substances that kill bacteria, but not necessarily viruses or fungi. "Disinfected" refers to a treatment with one or more substances that reduce or effectively eliminate viruses and fungi, in addition to bacteria. "Sterilization" refers to a treatment that destroys all microscopic life, and can include treatment by chemicals, heat, and/or radiation such as ultra-violet light.

In embodiments, this logged data is compared 502 with a pre-specified sanitation schedule to determine 504 if the logged sanitation events meet or exceed the requirements of the sanitation schedule. If so, then compliance with the sanitation schedule is recorded 506. If not, then corrective action is initiated, for example by informing management 508 as to a suspected failure to adhere to the required sanitation schedule.

Determining User Movement Patterns

Figure 6:
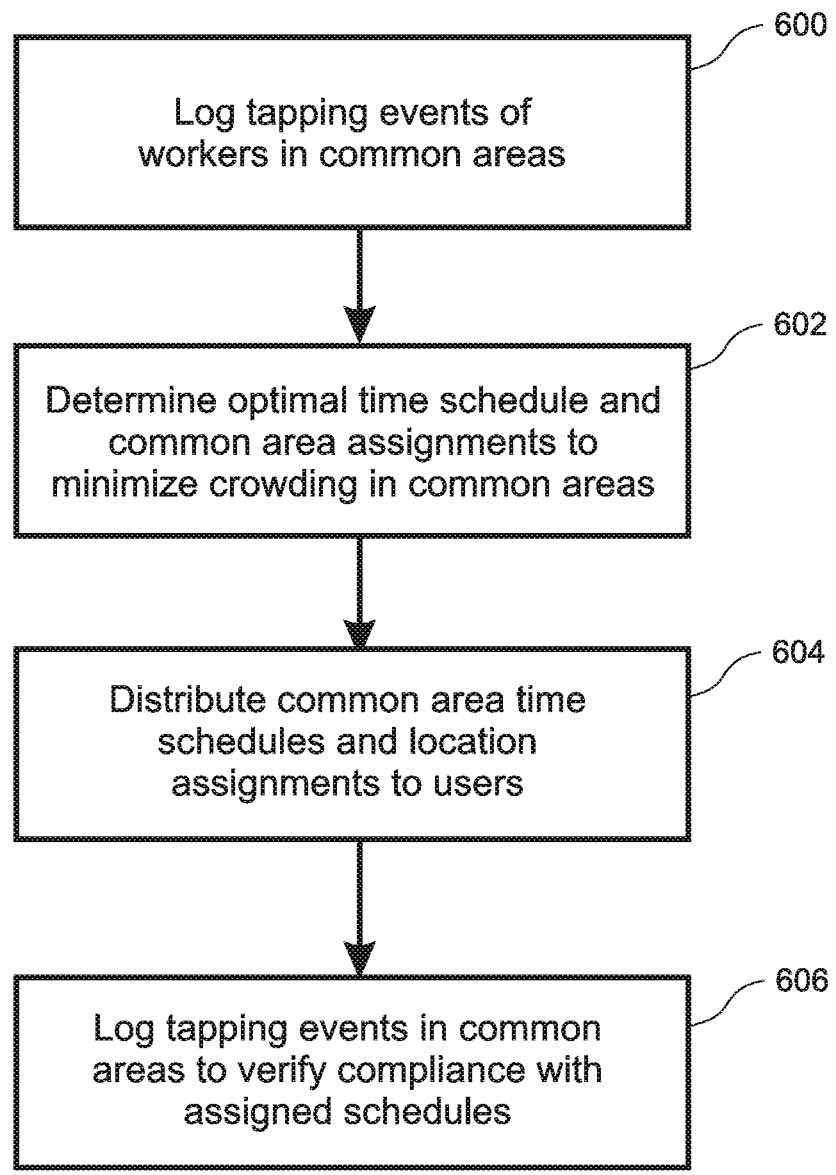
FIG. 6 is a flow diagram illustrating a method embodiment of the present invention wherein logged tapping events are used to establish and monitor compliance with location assignments and usage schedules assigned to users.

With reference to FIG. 6, in embodiments, during an initial tracking phase 600, users 110 are allowed to move between their workstations 104, bathrooms 200, corridors, dining facilities 302, and other common areas without restriction, and their movements are monitored according to the tapping events that are logged. The logged information is then used to determine optimal schedules and/or optimal assignments of common area locations 602 that will minimize crowding in those areas. For example, workers can be assigned 604 to use specific bathroom stalls, sinks, and cafeteria tables, and in some embodiments the use of certain facilities, such as cafeteria tables, can also be distributed over specified time periods, thereby ensuring that occupation of the common areas does not exceed maximum numbers, and that usage of common facilities such as bathroom stalls and cafeteria tables is evenly distributed.

Once optimal schedules and assignments have been distributed to the workers 604, subsequent tapping is used to log activity and can be used to monitor compliance with the location assignments and schedules 606.

In similar embodiments, after the initial tracking phase 600, users are only required to tap locations that are outside of their normal movement patterns. For example, during normal usage times a user may not need to continue tapping his or her desk and lunch table, which the user encounters at the same times each day, but may still be required to tap in at conference rooms when attending meetings that are not daily events. In some of these embodiments, a "geo-fence" approach can be used to determine if a user is present at the workplace on a given day, for example based on determining the user's location using "GPS" (global positioning system) location awareness.

Focusing Mitigation Efforts

Figure 7:
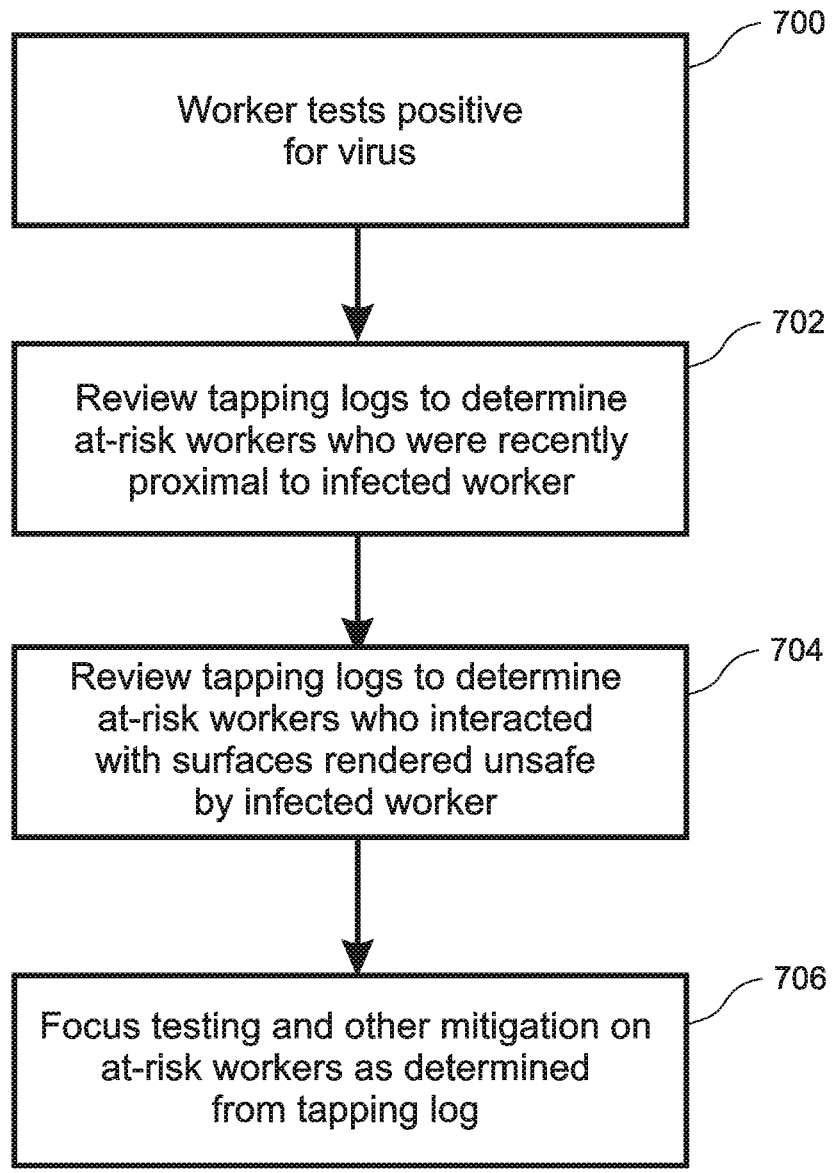
FIG. 7 is a flow diagram illustrating a method embodiment of the present invention wherein logged tapping events are used to enhance mitigation of an infection event by identifying users who are at heightened risk of cross-contamination.

With reference to FIG. 7, in embodiments, if a user is found to have been infected 700, the logged information can be used to enhance contact tracing by identifying at-risk workers who simultaneously occupied the same public spaces as the infected worker 702, such as by using the same bathroom at the same time, or occupying the same lunch table at the same time. In embodiments, air current patterns are assessed in common areas such as dining areas, bathrooms, and cubical "farms," and are used to estimate which of the personnel who were located in these areas are most likely to have been infected by air-born virus particles emitted by the infected user.

The logged information can further be reviewed to determine at-risk workers who may have had physical contact with surfaces in common areas shortly after they had been rendered high risk due to contact by the infected worker 704. These determinations will not necessarily be limited to common areas. For example, sanitation workers may be at risk if they sanitized a workstation that is assigned to the infected employee.

Once the at-risk employees have been identified, aggressive virus testing and/or other mitigation efforts such as precautionary quarantine can be focused on the at-risk employees 706, while other employees who are not deemed to be at high risk may be allowed to continue to perform their duties, either in whole or in part.

Defining "Sub-Groups" of Personnel

With reference again to FIG. 6, the step of determining optimal time schedules and location assignments for use of common areas 602 can be extended to create virtual sub-groups of workers who will come into limited contact with each other, either in person or via shared surfaces, but who will rarely come into contact with any other workers outside of their sub-group. This can be accomplished by assigning certain bathroom stalls, sinks, lunch tables, and other common areas to the same limited group of users, so that necessary interactions between workers are limited primarily to interactions within the defined sub-groups.

Accordingly, if a worker is found to be infected, testing and other mitigation efforts can be focused primarily on the other members of the infected user's sub-group. Furthermore, dividing the workforce into sub-groups in this matter can create virtual "firewalls" that can impede any spread of the infection within the workplace, whereby if there is any spread of infection, it will most likely be limited only to other personnel within the sub-group of the infected worker, or to only a few sub-groups, and is less likely to spread throughout the workforce as a whole.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

Although the present application is shown in a limited number of forms, the scope of the invention is not limited to just these forms, but is amenable to various changes and modifications without departing from the spirit thereof. The disclosure presented herein does not explicitly disclose all possible combinations of features that fall within the scope of the invention. The features disclosed herein for the various embodiments can generally be interchanged and combined into any combinations that are not self-contradictory without departing from the scope of the invention. In particular, the limitations presented in dependent claims below can be combined with their corresponding independent claims in any number and in any order without departing from the scope of this disclosure, unless the dependent claims are logically incompatible with each other.

We claim:

1. A method of minimizing cross-contamination of pathogens between protected persons located at a workplace and/or improving an efficacy of a response to a cross-contamination at the workplace, the method comprising:

locating a plurality of tags at selected tagged locations within the workplace;

selecting designated personnel from among personnel who are present at the workplace;

for each designated person of the designated personnel, causing the designated person to maintain a mobile device in the designated person's possession while the designated person is in the workplace, said mobile device being configured to interact with each of the tags during a tapping event when the mobile device is proximal to the tag;

at least one of the mobile devices and the tags being configured to accept input information provided by the designated personnel, said input information including information pertaining to a duration of time and information relevant to sanitation of the location where the tag is located, and to provide tapping information regarding said tapping events to a server, said tapping information including said input information; and according to an analysis of the tapping information, taking an action that reduces a risk of cross-contamination of pathogens between the protected persons who are present at the workplace by modifying at least one activity of at least one of the protected persons, and/or enhances an efficacy of a response to a cross-contamination at the workplace by identifying at least one of the protected persons who is at an enhanced risk of cross-contamination.

2. The method of claim 1, wherein the designated personnel include a majority of all of the personnel who are present at the workplace.

3. The method of claim 1, wherein the tapping information includes information pertaining to a duration of time during which the designated person was proximal to the tag.

4. The method of claim 1, wherein modifying the at least one activity of the at least one protected person includes causing a protected person to avoid a tagged location by designating the tagged location as being at elevated risk if, according to the tapping information:

the tagged location has not been sanitized since it was previously tapped by one of the designated persons; and insufficient time has elapsed since the tagged location was tapped by one of the designated persons to ensure that a specified percentage of any pathogens deposited at the tagged location have become non-infectious.

5. The method of claim 1, wherein modifying the at least one activity of the at least one protected person includes causing the protected person to adhere to sanitization requirements that are assigned to the protected person, if the analysis of the tapping information indicates non-compliance therewith.

6. The method of claim 1, wherein modifying the at least one activity of the at least one protected person includes directing the protected person to consistently use a designated facility from among a plurality of facilities that are within the workplace.

7. The method of claim 6, wherein the designated facility is selected from among the plurality of facilities according to an analysis of the tapping information obtained before the designated facility was selected.

8. The method of claim 6, wherein the method further comprises dividing the protected persons into a plurality of sub-groups, and assigning the plurality of facilities that are within the workplace to the subgroups, such that use of the same one of the facilities by members of more than one of the subgroups is minimized or eliminated.

9. The method of claim 8, wherein the plurality of facilities includes facilities that are located in a plurality of common areas.

10. The method of claim 1, wherein enhancing the efficacy of the response to the cross-contamination at the workplace includes, upon determining that a first protected person of the protected persons is infected with a pathogen, analyzing the tapping information to identify a second protected person of the protected persons who is at heightened risk of cross contamination of the pathogen by the first protected person, and applying at least one mitigating action to the second protected person.

11. The method of claim 10, wherein the mitigating action is applying a test to the second protected person to determine if the second protected persons has become infected with the pathogen.

12. The method of claim 10, wherein identifying the second protected person includes determining that the first and second protected persons occupied the same or proximal locations within the workplace at the same time.

13. The method of claim 12, wherein identifying the second protected person further includes determining a pattern of air currents proximal to the location or locations within the workplace that were occupied by the first and second protected persons at the same time.

14. The method of claim 10, wherein identifying the second protected person includes determining that the second protected person occupied a location that was previously occupied by the first protected person, said occupation by the second protected person being at a time when a heightened risk existed of cross contamination of the second protected person due to touching a surface that had previously been contaminated by the first protected person.

15. An apparatus for minimizing cross-contamination of pathogens between protected persons located at a workplace and/or improving an efficacy of a response to a cross-contamination at the workplace, the apparatus comprising:

a plurality of tags configured to be located at selected tagged locations within the workplace; and a plurality of mobile devices configured to interact with each of the tags during a tapping event when the mobile device is proximal to the tag;

the apparatus including at least one processor and a memory;

at least one of the mobile devices and the tags being configured to accept input information, said input information including information pertaining to a duration of time and information relevant to sanitation of the location where the tag is located, and to provide tapping information regarding said tapping events to a server, said tapping information including said input information; and The apparatus being configured for:

selecting personnel who are present at the workplace to be designated personnel;

for each designated person of the designated personnel, causing the designated person to maintain a mobile device in the designated person's possession while the designated person is in the workplace, said mobile device being configured to interact with each of the tags during a tapping event when the mobile device is proximal to the tag; and according to an analysis of the tapping information, taking an action that reduces a risk of cross-contamination of pathogens between the protected persons who are present at the workplace by modifying at least one activity of at least one of the protected persons, and/or enhances an efficacy of a response to a cross-contamination at the workplace by identifying at least one of the protected persons who is at an enhanced risk of cross-contamination.

16. The apparatus of claim 15, wherein the tags are powered devices.

17. The apparatus of claim 16, wherein the tags are configured to communicate with the mobile devices by Bluetooth communication.

18. The apparatus of claim 15, wherein the tags include optically scannable indicia.

19. The apparatus of claim 15, wherein the tags are unpowered.

20. The apparatus of claim 19, wherein the tags are configured to communicate with the mobile devices by near field communication.

21. A system configured for minimizing cross-contamination of pathogens between protected persons located at a workplace and/or improving an efficacy of a response to a cross-contamination at the workplace, the system comprising:
  a plurality of tags configured to be located at selected tagged locations within the workplace;
  a plurality of mobile devices configured to interact with each of the tags during a tapping event when the mobile device is proximal to the tag; and
  a server configured to communicate with at least one of the tags and the mobile devices;
  the system including at least one processor and a memory;
  at least one of the mobile devices and the tags being configured to accept input information, said input information including information pertaining to a duration of time and information relevant to sanitation of the location where the tag is located, and to provide tapping information regarding said tapping events to the server, said tapping information including said input information; and
The system being configured for:
  selecting personnel who are present at the workplace to be designated personnel;
  for each designated person of the designated personnel, causing the designated person to maintain a mobile device in the designated person's possession while the designated person is in the workplace, said mobile device being configured to interact with each of the tags during a tapping event when the mobile device is proximal to the tag; and
  according to an analysis of the tapping information, taking an action that reduces a risk of cross-contamination of pathogens between the protected persons who are present at the workplace by modifying at least one activity of at least one of the protected persons, and/or enhances an efficacy of a response to a cross-contamination at the workplace by identifying at least one of the protected persons who is at an enhanced risk of cross-contamination.

* * * * *